United States Patent [19]

Rand

[11] 4,346,612
[45] Aug. 31, 1982

[54] LIQUID SAMPLER
[75] Inventor: John H. Rand, Cornish, N.H.
[73] Assignee: The United States of America as represented by the Secretary of the Army, Washington, D.C.
[21] Appl. No.: 248,934
[22] Filed: Mar. 30, 1981
[51] Int. Cl.³ .......................... G01N 1/08; G01N 1/12
[52] U.S. Cl. .................................. 73/864.44; 73/864.63
[58] Field of Search ............ 73/864.44, 864.63, 864.44

[56] References Cited

U.S. PATENT DOCUMENTS

| | | | |
|---|---|---|---|
| 892,944 | 7/1908 | Drawe | 73/87.63 |
| 2,434,835 | 1/1948 | Colley | 138/45 |
| 2,436,737 | 2/1948 | White et al. | 73/864.65 |
| 2,515,882 | 7/1950 | McClusky | 73/864.65 |
| 2,746,225 | 5/1956 | Cloud | 53/370 |
| 2,846,179 | 8/1958 | Monckton | 251/4 |
| 3,383,131 | 5/1968 | Rosfelder | 73/864.44 |
| 3,504,550 | 4/1970 | Koch et al. | 73/864.65 |
| 3,807,234 | 4/1974 | Duperon | 175/248 |
| 4,106,576 | 10/1977 | Clements | 73/864.44 |

Primary Examiner—S. Clement Swisher
Attorney, Agent, or Firm—Darrell E. Hollis

[57] ABSTRACT

A liquid sampler, and particularly, a liquid sampler for sampling liquid containing frazil ice, employs a sampling tube open at both top and bottom which can be thrust into the liquid to be sampled and a membrane-type cylindrical valve which is closed by pulling a single string which is looped about the cylindrical membrane. A cutting shoe at the lower end of the sampling tube permits cutting through ice for obtaining the sample.

3 Claims, 1 Drawing Figure

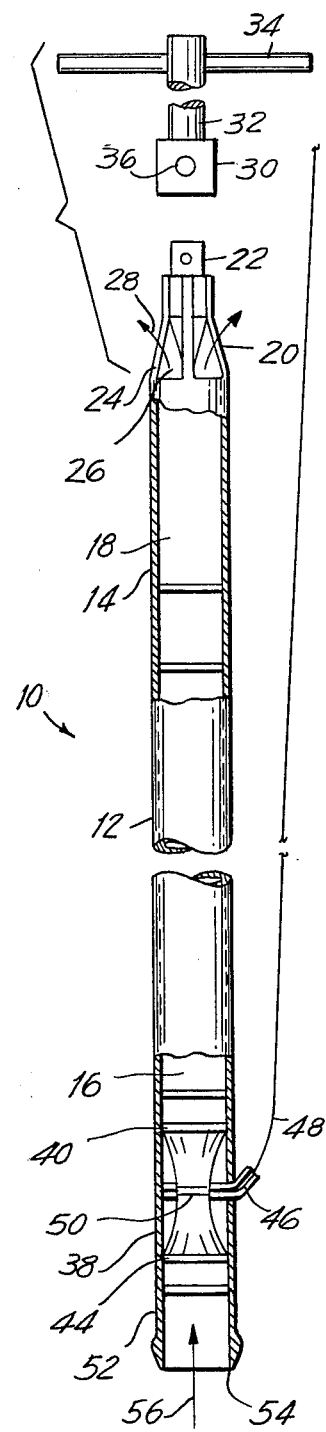

LIQUID SAMPLER

STATEMENT OF GOVERNMENT INTEREST

The invention described and claimed herein may be manufactured and used by or for the Government of the United States of America for governmental purposes without the payment of royalties thereon or therefor.

BACKGROUND OF THE INVENTION

The present invention relates to sampling tubes and, more particularly, to sampling tubes adapted for obtaining samples of liquid containing frazil ice.

Obtaining samples of frazil ice for research and analysis into its effect on, for example, hydroelectric power plants, has presented a number of problems. Most of these problems arise due to the failure to provide a liquid sampler which can quickly obtain a sample which contains a true representation of the frazil ice in the area being analyzed.

Sampling devices such as disclosed in U.S. Pats. Nos. 3,504,550; 3,807,234; 2,515,882; 2,436,737 and 892,944 comprise hollow cylindrical samplers initially open at both top and bottom which are lowered to the desired depth whereupon the bottom of the sample tube is closed and the entire unit raised to the surface.

For collecting frazil ice samples, the apparatus disclosed in the above noted patents fail to collect total samples representative of the area. In an attempt to obtain satisfactory samples, it has been necessary at times to chop large diameter holes in the ice to allow a diver to go under the ice and sample from the bottom up.

OBJECTS AND SUMMARY OF THE INVENTION

Accordingly, it is an object of the present invention to provide a liquid sampler which overcomes the above noted drawbacks.

It is a further object of the invention to provide a liquid sampler adapted for obtaining samples of frazil ice.

It is a further object of the invention to provide a liquid sampler having a cutting shoe at the bottom, a cylindrical membrane-type valve actuated by a string and a sampling tube which are assembleable into an integral unit and which may be lowered to obtain a sample of liquid and/or frazil ice.

According to an aspect of the invention there is provided a sampler comprising a hollow cylindrical sampling tube having a top and a bottom, valve means affixed at the bottom of the sampling tube, a cylindrical cutting shoe having a top and a bottom, the top of the cutting shoe being affixed to the valve means, the bottom of the cutting shoe being sharpened, adapter means for connecting an extension to the top of the sampling tube, the adapter means being effective to permit substantially free flow of fluid axially therethrough, the valve means including a cylindrical membrane having a first condition wherein it conforms to a substantially cylindrical shape permitting substantially free fluid communication therethrough and having a second condition wherein it assumes a closed hourglass shape permitting substantially no fluid communication therethrough, the valve means further including a body having a string guide therethrough, a string affixed at a first end to the body, a loop in the string encircling the cylindrical membrane and the string passing through the string guide, and the loop, when tightened by pulling the string, producing the second condition.

The above, and other objects, features and advantages of the present invention will become apparent from the following description read in conjunction with the accompanying drawings, in which like reference numerals designate the same elements.

BRIEF DESCRIPTION OF THE DRAWING

FIG. 1 is a side view, partially in cross section, of a liquid sampler according to an embodiment of the invention.

DETAILED DESCRIPTION OF THE PREFERRED EMBODIMENTS

Referring now to FIG. 1, there is shown, generally at 10 an embodiment of a liquid sampler according to the present invention.

A sampling tube 12, which may be of any suitable material but is preferably of plastic, is connected by any suitable means such as, for example, by threaded connection to the top adapter 14 having a diameter substantially equal to the diameter of sampling tube 12.

Sampling tube 12 has a cylindrical inner cavity 16 which opens into a matching cylindrical inner cavity 18 in top adapter 14.

Top adapter 14 is joined by a spider 20 to an extension adapter 22. Spider 20 is seen to consist of a plurality of metal strips 24 either attached to or integrally formed with top adapter 14 and providing substantial clear openings 26 therebetween to provide substantially free flow of fluid out of sampling tube 12 and top adapter 14 as indicated by flow arrows 28.

Extension adapter 22 may have any convenient form such as, for example, the circular shape shown. An extension fitting 30 may be provided for engagement with extension adapter 22. Extension fitting 30 is affixed to the lower end of an extension rod 32 of any convenient length which may have a Tee handle 34 at its upper end. A push pin 36, or other attachment means may be employed to securely attach extension fitting 30 over extension adapter 22 to prevent loss of liquid sampler 10.

It would be clear to one skilled in the art that either a single extension rod 32, or a plurality of end-connected extension rods may be employed to extend sampling tube 12 to any necessary depth.

A valve section 38 is affixed by any convenient means such as, for example, by threaded connection (not shown in FIG. 1) to the bottom of sampling tube 12. A cylindrical membrane 40, which is preferably of resilient material, and most preferably of rubber is stretched between an upper ring 42 and a lower ring 44.

A string guide 46 is centrally disposed in the wall of valve section 38 to guide a string 48 therethrough. String 48 forms a loop 50 of at least one turn about cylindrical membrane 40 and has its end anchored to valve section 38.

A cutting shoe 52 is affixed by any convenient means such as, for example, by threaded connection below valve section 38. Cutting shoe 52 has a sharpened lower end 54 to enable cutting through frazil ice accumulations to thus obtain a true sample of the frazil ice which lies within the perimeter of sharpened lower end 54 and to exclude portion lying outside that perimeter.

When string 48 is loosened, loop 50 enlarges to permit cylindrical membrane 40 to lie substantially flat against the cylindrical inner surface of valve section 38. In this condition, a substantially free flow of water and ice crystals is permitted to enter lower end 54 of cutting shoe 52 as indicated by an arrow 56 and to pass substantially unimpeded through valve section 38, sampling tube 12 and top adapter 14 and to exit through openings 26. Thus, liquid sampler 10 may be lowered to any desired depth during which lowering process the liquid and other matter in the lowering path passes into, through and out of liquid sampler 10. When the desired depth is attained, string 48 is pulled. At an intermediate amount of pull on string 48, cylindrical membrane 40 assumes the generally hourglass shape shown. When fully pulled, string 48 completely closes cylindrical membrane 40 to trap the contents of sampling tube 12 therein.

In the embodiment shown, string 48 must be maintained taut while liquid sampler 10 is raised to the surface. It would be within the contemplation of the present invention to provide means for holding loop 50 closed once this has been accomplished by pulling string 48.

Having described specific embodiments of the invention with respect to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A sampler comprising:
   a hollow cylindrical sampling tube having a top and a bottom; valve means affixed at the bottom of said sampling tube;
   a cylindrical cutting shoe having a top and a bottom;
   the top of said cutting shoe being affixed to said valve means;
   the bottom of said cutting shoe being sharpened;
   adapter means for connecting an extension to the top of said sampling tube;
   said adapter means being effective to permit substantially free flow of fluid axially therethrough;
   said valve means including a cylindrical membrane having a first condition wherein it conforms to a substantially cylindrical shape permitting substantially free fluid communication therethrough and having a second condition wherein it assumes a closed hourglass shape permitting substantially no fluid communication therethrough;
   said valve means further including a body having a string guide therethrough, a string affixed at a first end to said body, a loop in said string encircling said cylindrical membrane and said string passing through said string guide; and
   said loop, when tightened by pulling said string, producing said second condition.

2. A sample according to claim 1 wherein said adapter means includes a tube affixed to the top of said sampling tube and an extension adapter to which an extension rod may be connected, said extension adapter being connected to said tube by a spider, said spider defining openings which permit substantially free flow of fluid therethrough from said tube.

3. A sample according to claim 1 wherein said valve means includes an upper ring for clamping an upper end of said cylindrical membrane into a first open circle and a lower ring for clamping a lower end of said cylindrical membrane into an open circle.

* * * * *